(12) United States Patent
Geremia et al.

(10) Patent No.: US 6,414,004 B1
(45) Date of Patent: Jul. 2, 2002

(54) 3-SUBSTITUTED 5-ARYL-4-ISOXAZOLECARBONITRILES HAVING ANTIVIRAL ACTIVITY

(75) Inventors: Ernesto Geremia; Gianna Tempera; Angelo Castro; Adriana Garozzo; Francesco Guerrera; Rossella Maria Campagna, all of Catania (IT)

(73) Assignee: Universita' Degli Studi di Catania, Catania (IT)

( * ) Notice: Subject to any disclaimer, the term of this patent is extended or adjusted under 35 U.S.C. 154(b) by 0 days.

(21) Appl. No.: 09/708,857
(22) PCT Filed: May 7, 1999
(86) PCT No.: PCT/EP99/03153
§ 371 (c)(1), (2), (4) Date: Dec. 21, 2000
(87) PCT Pub. No.: WO99/59984
PCT Pub. Date: Nov. 25, 1999

(30) Foreign Application Priority Data

May 15, 1998 (IT) .......................................... MI98A1072

(51) Int. Cl.⁷ ........................ A61K 31/42; C07D 261/06
(52) U.S. Cl. ...................................... 514/380; 548/247
(58) Field of Search ........................... 548/247; 514/380

(56) References Cited

PUBLICATIONS

Campagne et al. Isoxazoles with Antiviral Activity. First Italiam Swiss Meeting on Medicinal Chemistry, (Turin, 1997), 206.*

* cited by examiner

Primary Examiner—Joseph K. McKane
Assistant Examiner—Rebecca Anderson
(74) Attorney, Agent, or Firm—Walter H. Schneider

(57) ABSTRACT

3-Substituted-5-Aryl-4-Isoxazolecarboritriles having antiviral activity.

7 Claims, No Drawings

3-SUBSTITUTED 5-ARYL-4-ISOXAZOLECARBONITRILES HAVING ANTIVIRAL ACTIVITY

This is a 371 of international application PCT/EP99/03153 with international filing date of May 7, 1991 published in English.

The invention relates to compounds with a 3-substituted 5-aryl-4-isoxazolecarbonitrile structure, of formula (I)

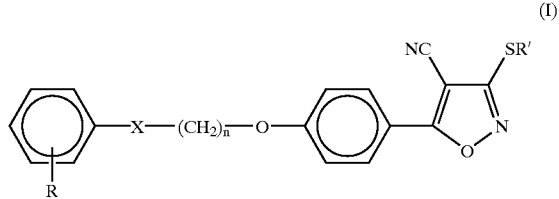

wherein
- R is hydrogen, halogen, COOH, COOR'', $C_1$–$C_4$ alkyl, $NO_2$, OR'', phenyl;
- R' is $C_1$–$C_4$ alkyl, COOH, COOR'';
- R'' is $C_1$–$C_4$ alkyl;
- X is an oxygen or sulfur atom or a single bond;
- n is an integer 1–6,
  with the proviso that, when R' is $CH_3$, R is different from hydrogen;
  said compounds having antiviral activity.

In Acts of the First Italian-Swiss Meeting of Medicinal Chemistry (Turin, 1997) derivatives of formula (I) with R=H and R'=$CH_3$ supposedly having antiviral activity, are cited. It has now been found that both said derivatives and those of formula (I) with R different from hydrogen, have indeed antiviral activity which is of great interest as far as a series of viruses, are concerned.

The invention also relates to pharmaceutical compositions containing as active ingredient at least one compound of formula (I) wherein R', R'', X and n have the meanings defined above, whereas R is hydrogen, also when R'=$CH_3$, optionally combined with one or more other active principles.

Preferred compounds of formula (I) in the compositions according to the invention are those wherein R is hydrogen, bromine, COOH, COOCH$_3$, CH$_3$, NO$_2$; R' is CH$_3$; X is an oxygen atom; n is 2, 3 or 4. Particularly preferred are those compounds wherein R is at the 4-position on the phenyl ring.

According to the invention, compounds (I) are obtained by reacting an intermediate of formula (II) with a 5-(4-hydroxyphenyl)-4-isoxazolecarbonitrile having a R'S substituent at the 3-position, for example with 3-methylthio-5-(4-hydroxyphenyl)-4-isoxazolecarbonitrile (III), according to scheme A shown hereinbelow:

Scheme A

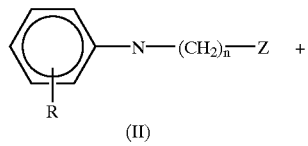

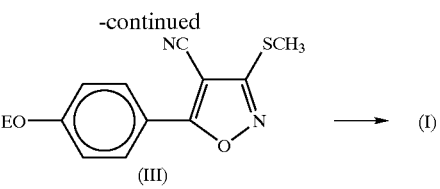

wherein R, X and n have the meanings defined above, whereas Z is a halogen atom, preferably a bromine atom.

Intermediate (III) is obtained following scheme B; intermediates of formula (III) wherein the methyl group is substituted by carboxyl or carbalkoxyl can be prepared analogously,

SCHEME B

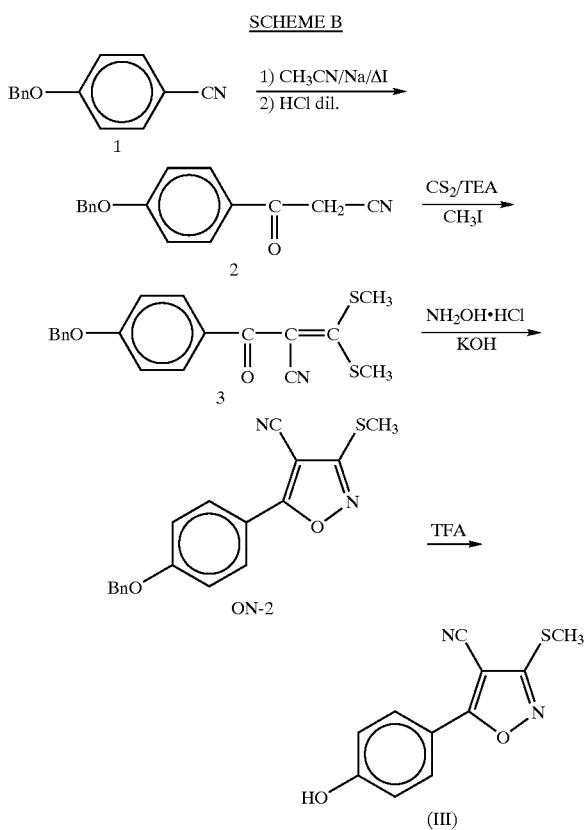

whereas intermediates (II) can be prepared according to per se known methods.

The reaction yielding final compounds (I), according to scheme A, is suitably carried out in the presence of an acid-binding agent, for example potassium carbonate, in inert solvents, at temperatures ranging from room temperature to about 100° C. Suitable solvents are, for example, ketones such as acetone, methyl ethyl ketone, methyl isopropyl ketone, or ethers such as tetrahydrofuran or dioxane.

The following examples illustrate the process according to the invention.

EXAMPLE 1

3-Methylthio-5-(4-hydroxyphenyl)-4-isoxazolecarbonitrile (III)

a) 1.5 mol of 4-benzyloxy-benzonitrile (1) and 2 mol of $CH_3CN$ were dissolved in anhydrous. ether (T. Naito et al., Bull. Chem. Soc. of Japan, 1968, 41, 959). After adding an equimolar amount of metallic sodium hot powdered in toluene, the mixture was refluxed for about 24 h. The resulting solid was separated by filtration, repeatedly washed with ether, then poured into ice-water. The aqueous suspension of the resulting product (4-benzyloxy-β-aminocinnamonitrile) was neutralized with concentrated HCl, acidified with 2N HCl and stirred for 24 h at room temperature until complete hydrolysis of the product. 1 mol of the resulting 4-benzyloxy-cyanoacetophenone (2) was reacted with 1 mol of $CS_2$ in DMF and 1 mol of triethylamine; after 15 min stirring at room temperature, a $CH_3I$ excess was added therein to obtain the corresponding acylketene-S,S-acetal (3).

0.01 mol of this compound were cyclized in the presence of $N_2OH.HCl$ (0.025 mol) and KOH (0.025 mol) (Rudorf W. D. et al.; J. Pratk. Chemie., 1978, 320. 585).

The resulting 3-methylthio-5-(4-benzyloxyphenyl)-4-isoxazolecarbonitrile (ON-2) was filtered and crystallized from ethanol. Yield 84%; m.p. 178–179° C. (ethanol); IR (KBr) 2227 (CN) $cm^{-1}$; $^1H$ NMR ($CDCl_3$) (δ, ppm) 2.67 (s, 3H, $SCH_3$); 5.15 (s, 2H, Ph—$CH_2$—O); 7.08–8.01 (m, 4H, arom.); 7.37–7.44 (m, 5H, arom.).

b) 34 mmol of ON-2, 1.5 ml of thioanisole and 5 ml of TFA were stirred at room temperature for 24 h. The suspension was then dissolved in hot ethanol and poured into ice-water. The precipitate was filtered, washed to neutral pH with a $NaHCO_3$ solution and crystallized from acetonitrile to obtain 3-methylthio-5-(4-hydroxyphenyl)-4-isoxazolecarbonitrile (III). Yield 76%; m.p. 194–196° C. (acetonitrile); IR (KBr) 3330 (broad, OH), 2233 (CN) $cm^{-1}$; $^1H$ NMR (DMSO) (δ, ppm) 2.67 (s, 3H, $SCH_3$); 3.18 (s, 1H, OH); 6.8–7.7 (m, 4H, arom.).

EXAMPLE 2

3-Methylthio-5-[4-(2-phenyl-1-ethoxy)-phenyl]-4-isoxazolecarbonitrile (ON-6)

Equimolecular amounts of (III), 2-phenyl-ethyl bromide and $K_2CO_3$ were refluxed in acetone for 48 h. The mixture was concentrated to small volume and shaken with diethyl ether and water. The ether phase was washed with 2 M NaOH, then with water, evaporated to dryness and the residue was recrystallized from ethanol. The title product was obtained in an 80% yield (abbreviation ON-6), m.p. 93–940° C. (ethanol); IR (KBr) 2227 (CN) $cm^1$; $^1H$ NMR ($CDCl_3$) (δ, ppm) 2.66 (s, 3H, $SCH_3$); 3.14 (t, 2H, $CH_2$—Ph); 4.26 (t, 2H, O—$CH_2$); 7.30 (m, 5H, arom.); 6.99–8.00 (m, 4H, arom.).

EXAMPLES 3–10

Analogously to the procedure described in example 2, the following compounds of general formula (I) were obtained:

3-Methylthio-5-[4-(3-phenyl-1-propoxy)-phenyl]-4-isoxazolecarbonitrile ON-7

Yield: 88%; m.p. 99–100° C. (ethanol); IR (KBr) 2228 (CN) $cm^{-1}$; $^1H$ NMR ($CDCl_3$) (δ, ppm) 2.11–2.18 (m, 2H, $CH_2$—$CH_2$—$CH_2Ph$); 2.67 (s, 3H, $SCH_3$); 2.83 (t, 2H, $CH_2$—Ph); 4.04 (t, 2H, O—$CH_2$); 7.24 (m, 5H, arom.); 6.98–8.00 (m, 4H, arom.).

3-Methylthio-5-[4-(2-phenoxy-1-ethoxy)-phenyl]-4-isoxazolecarbonitrile ON-8

Yield: 80%; m.p. 128–131° C. (ethanol); IR (KBr) 2227 (CN) $cm^{-1}$; $^1H$ NMR ($CDCl_3$) (δ, ppm) 2.67 (s, 3H, $SCH_3$); 4.36–4.42 (m, 4H, $OCH_2CH_2O$); 6.93–7.35 (m, 5H, arom.); 7.07–8.03 (m, 4H, arom.).

3-Methylthio-5-[4-(3-phenoxy-1-propoxy)-phenyl]-4-isoxazolecarbonitrile ON-9

Yield: 90%; m.p. 121–123° C. (ethanol); IR (KBr) 2227 (CN) $cm^{-1}$; $^1H$ NMR ($CDCl_1$) (δ, ppm) 2.27 (m, 2H, $CH_2$—$CH_2$—$CH_2$); 2.66 (s, 3H, $SCH_3$); 4.17 (t, 2H, $OCH_2$—Ph); 4.26 (t, 2H, $OCH_2$—Ph-isox); 6.89–7.33 (m, 5H, arom.); 6.95–8.01 (m, 4H, arom.).

3-Methylthio-5-[4-(4-phenoxy-1-butoxy)-phenyl]-4-isoxazolecarbonitrile ON-10

Yield: 91%; m.p. 113–114°C. (ethanol); IR (KBr) 2226 (CN) $cm^{-1}$; $^1H$ NMR ($CDCl_3$) (δ, ppm) 2.01 (t, 4H, $CH_2$—$CH_2$); 2.67 (s, 3H, $SCH_3$); 4.05 (t, 2H, $OCH_2$—Ph); 4.13 (t, 2H, $OCH_2$—Ph-isox); 6.87–7.33 (m, 5H, arom.); 6.92–8.01 (m, 4H, arom.).

3-Methylthio-5-[4-[2-(4-nitrophenoxy)ethoxy]phenyl]-4-isoxazolecarbonitrile ON-11

Yield: 82%; m.p. 170–171°C. (acetonitrile); IR (KBr) 2234 (CN), 1252 ($NO_2$) $cm^{-1}$; $^1H$ NMR ($CDCl_3$) (δ, ppm) 2.68 (s, 3H, $SCH_3$); 4.46 (s, 4H, $OCH_2CH_2O$); 7.01–7.11 (m, 4H, arom, Ph-isox); 8.00–8.26 (m, 4H, arom., Ph—$NO_2$).

3-Methylthio-5-[4-[2-(4-methylphenoxy)ethoxy]phenyl]-4-isoxazolecarbonitrile ON-12

Yield: 70%; m.p. 139–140° C. (acetonitrile); IR (KBr) 2232 (CN) $cm^{-1}$; $^1H$ NMR ($CDCl_3$) (δ, ppm) 2.29 (s, 3H, Ph—$CH_3$); 2.67 (s, 3H, $SCH_3$); 4.33–4.40 (m, 4H, $OCH_2CH_2O$) 6.83–8.03 (m, 4H, arom., Ph-isox); 7.06–7.25 (m, 4H, arom., Ph—$CH_3$).

Ethyl-4-[[2-[4-(3-methylthio-4-cyano-5-isoxazolyl)-phenoxy]-ethyl]-oxy]benzoate ON-13

Yield: 74%; m.p. 162–164° C. (acetonitrile); IR (KBr) 2232 (CN); 1711 ($COOC_2H_5$) $cm^{-1}$; $^1H$ NMR ($CDCl_3$) (δ, ppm) 1.39 (t, 3H, $COOCH_2CH_3$); 2.67 (s, 3H, $SCH_3$); 4.30–4.41 (m, 4H, $OCH_2CH_2O$); 4.42 (s, 2H, $COOCH_2CH_3$); 6.95–7.11 (m, 4H, arom., Ph-isox); 7.99–8.04 (m, 4H, arom., Ph—$COOC_2H_5$).

3-Methylthio-5-[4-[2-(4-bromophenoxy)ethoxy]phenyl]-4-isoxazolecarbonitrile ON-14

Yield: 76%; m.p. 156–157° C. (acetonitrile); IR (KBr) 2230 (CN); 1660 (broad, Br) $cm^{-1}$; $^1H$ NMR ($CDCl_3$) (δ, ppm) 2.67 (s, 3H, $SCH_3$); 4.30–4.42 (m, 4H, $OCH_2CH_2O$); 6.81–7.42 (m, 4H, arom., Ph—Br); 7.06–8.03 (m, 4H, arom., Ph-isox).

For the in vitro tests the compounds were solubilised in DMSO and subsequently diluted in Eagle's Minimum Essential medium.

The compounds of the invention proved to have high antiviral activity. As it will be shown in the following, said activity is exerted, at non-cytotoxic doses, against Polio 1, ECHO 9, Coxsackie $B_1$, Rhinovirus and Measles viruses. In particular, the antiviral activity of the compounds obtained according to examples 2–10 was tested as follows.

Viruses and Cells

The following types of RNA viruses were used: Polio 1 (Brunhilde strain), ECHO 9 (ATCC: VR-133), Coxsackie is $B_1$ (ATCC: VR-28), Measles (Edmonston strain) and various Rhinovirus serotypes (HRV2, HRV9, HRV14, HRV15, HRV29, HRV70, HRV86, HRV89, HRV 1B).

Viral stocks (for Polio 1, ECHO 9, Coxsackie $B_1$, Measles viruses) were prepared infecting at 37° C. semiconfluent mono-layers of HEp-2 cells in D-MEM medium without foetal bovine serum.

After the onset of the cytopathic effect, the cultures were frozen at −80° C. prior to use. The infectant viral titre was determined according to the plaque method (A. Garozzo et al., *Antiviral Res.*, 1990. 14, 267) and expressed as plaque forming units (PFU) per millilitre.

All cells were cultured in Eagle's Minimum Essential medium (Dulbecco modified: D-MEM) added with 6% inactivated foetal bovine serum (FCS), 200 µg of streptomycin and 200 U of penicillin G per ml.

Rhinoviruses were prepared infecting semiconfluent mono-layers of HeLa-Ohio cells in MEM added with 2% FCS, at 33° C. HeLa cells were cultured in Eagle's Mimimum Essential medium (MEM) added with 10% inactivated foetal bovine serum (FCS), 200 µg of streptomycin and 200 U of penicillin G per ml.

Cytotoxicity

The cytotoxicity of each substance was determined by direct observation under microscope, and mitochondrial dehydrogenases activities were assayed according to the MTT test (F. Denizot et al., *Immunol. Methods*, 1986, 89, 271).

The concentration of compound which, after 48–72 h of incubation at 37° C., inhibited by 50% the cell proliferation was defined as cytotoxic dose 50% ($CD_{50}$).

Antiviral Activity

The in vitro antiviral activity was evaluated according to the test of the direct inhibition of the plaques number (M. R. Pinizzotto et al., *Antiviral Res.* 1992, 19, 29).

Confluent mono-layers of cells in 24-well plates were infected with 200 PFU/ml of virus; after 1 h of virus adsorption at 37° C., medium with or without various doses of the tested substances was added.

When plaques were evident in the control virus (24–48 h), the cultures were stained with 1% crystal violet in methanol.

The percent reduction in the number of plaques compared with the control virus was evaluated for each sample.

The antiviral activity of Rhinoviruses was evaluated by reduction in the cytopathic effect in HeLa- Ohio cells, according to the MTT test (K. Andries et al., *Antimicrob. Agents Chemother.*, 1992 36(1), 100).

For each compound was calculated the percent reduction in the cytopathic effect compared with an untreated control.

Statistical Analysis

All the data are the mean values of three independent experiments with a standard deviation lower than 10%.

RESULTS

ON-6
Concentration Inhibiting by 50%
HEp$_2$ Cell Proliferation: $CD_{50}>20$ µM

| Active against | Concentration inhibiting by 100% viral replication (µM) |
|---|---|
| Polio 1 | 0.2 |
| ECHO 9 | 0.2 |
| Measles | 1 |
| Coxsackie $B_1$ | 10 |

Concentration inhibiting by 50%
HeLa Cell Proliferation: $CD_{50}>20$ µM

| Types of Rhinovirus | Concentration inhibiting by 100% viral replication (µM) |
|---|---|
| HRV-2 | 4 |
| HRV-9 | 8 |
| HRV-15 | 6 |
| HRV-29 | 2 |
| HRV-70 | 10 |
| HRV-86 | 6 |
| HRV-89 | 2 |
| HRV-1B | 5 |

ON-7
Concentration Inhibiting by 50%
HEp$_2$ Cell Proliferation: $CD_{50}>25$ µM

| Active against | Concentration inhibiting by 100% viral replication (µM) |
|---|---|
| Polio 1 | 0.4 |
| ECHO 9 | 0.2 |
| Measles | 10 |
| Coxsackie $B_1$ | 0.6 |

Concentration Inhibiting by 50%
HeLa Cell Proliferation: $CD_{50}>25$ µM

| Types of Rhinovirus | Concentration inhibiting by 100% viral replication (µM) |
|---|---|
| HRV-29 | 5 |
| HRV-70 | 5 |
| HRV-86 | 5 |
| HRV-89 | 5 |
| HRV-1B | 5 |

ON-8
Concentration Inhibiting by 50%
HEp$_2$ Cell Proliferation: $CD_{50}>25$ µM

| Active against | Concentration inhibiting by 100% viral replication (µM) |
|---|---|
| Polio 1 | 10 |
| ECHO 9 | 0.2 |
| Coxsackie $B_1$ | 10 |

Concentration Inhibiting by 50%
HeLa Cell Proliferation: $CD_{50}>25$ µM

| Types of Rhinovirus | Concentration inhibiting by 100% viral replication (µM) |
|---|---|
| HRV-70 | 5 |
| HRV-86 | 5 |
| HRV-89 | 5 |
| HRV-1B | 5 |

ON-9

Concentration Inhibiting by 50%

HEp2 Cell Proliferation: $CD_{50}=20\ \mu M$

| Active against | Concentration inhibiting by 100% viral replication ($\mu M$) |
|---|---|
| ECHO 9 | 0.1 |
| Measles | 10 |
| Coxsackie $B_1$ | 1 |

Concentration Inhibiting by 50%

HeLa Cell Proliferation: $CD_{50}=20\ \mu M$

| Types of Rhinovirus | Concentration inhibiting by 100% viral replication ($\mu M$) |
|---|---|
| HRV-70 | 5 |
| HRV-86 | 5 |
| HRV-89 | 5 |
| HRV-1B | 10 |

ON-10

Concentration Inhibiting by 50%

$HEp_2$ Cell Proliferation: $CD_{50}=10\ \mu M$

| Active against | Concentration inhibiting by 100% viral replication ($\mu M$) |
|---|---|
| ECHO 9 | 1 |
| Measles | 0.02 |
| Coxsackie $B_1$ | 0.02 |

Concentration Inhibiting by 50%

HeLa Cell Proliferation: $CD_{50}=10\ \mu M$

| Types of Rhinovirus | Concentration inhibiting by 100% viral replication ($\mu M$) |
|---|---|
| HRV-14 | 1 |
| HRV-29 | 1 |
| HRV-70 | 1 |
| HRV-86 | 1 |
| HRV-89 | 1 |
| HRV-1B | 2 |

ON-11

Concentration Inhibiting by 50%

$HEp_2$ Cell Proliferation: $CD_{50}=25\ \mu M$

| Active against | Concentration inhibiting by 100% viral replication ($\mu M$) |
|---|---|
| ECHO 9 | 4 |
| Measles | 10 |
| Coxsackie $B_1$ | 10 |

Concentration Inhibiting by 50%

HeLa Cell Proliferation: $CD_{50}=10\ \mu M$

| Types of Rhinovirus | Concentration inhibiting by 100% viral replication ($\mu M$) |
|---|---|
| HRV-70 | 8 |
| HRV-86 | 2 |

ON-12

Concentration inhibiting by 50%

HEp2 Cell Proliferation: $CD_{50}>25\ \mu M$

| Active against | Concentration inhibiting by 100% viral replication ($\mu M$) |
|---|---|
| Polio 1 | 1 |
| ECHO 9 | 0.06 |
| Measles | 10 |
| Coxsackie $B_1$ | 10 |

Concentration inhibiting by 50%

HeLa Cell Proliferation: $CD_{50}>25\ \mu M$

| Types of Rhinovirus | Concentration inhibiting by 100% viral replication ($\mu M$) |
|---|---|
| HRV-70 | 5 |
| HRV-86 | 5 |
| HRV-89 | 5 |

ON-13

Concentration Inhibiting by 50%

$HEp_2$ Cell Proliferation: $CD_{50}=25\ \mu M$

| Active against | Concentration inhibiting by 100% viral replication ($\mu M$) |
|---|---|
| Polio 1 | 10 |
| Measles | 0.2 |
| Coxsackie $B_1$ | 0.1 |

Concentration Inhibiting by 50%

HeLa Cell Proliferation: $CD_{50}=10\ \mu M$

| Types of Rhinovirus | Concentration inhibiting by 100% viral replication ($\mu M$) |
|---|---|
| HRV-14 | 2 |
| HRV-70 | 1 |
| HRV-86 | 1 |

ON-14
Concentration Inhibiting by 50%
HEp2 Cell Proliferation: $CD_{50} > 25$ $\mu M$

| Active against | Concentration inhibiting by 100% viral replication ($\mu M$) |
|---|---|
| Polio 1 | 1 |
| ECHO 9 | 0.06 |
| Measles | 0.2 |
| Coxsackie $B_1$ | 0.06 |

Concentration inhibiting by 50%
HeLa Cell Proliferation: $CD_{50} = 10$ $\mu M$

| Types of Rhinovirus | Concentration inhibiting by 100% viral replication ($\mu M$) |
|---|---|
| HRV-14 | 2 |
| HRV-70 | 2 |
| HRV-86 | 2 |
| HRV-89 | 2 |

As already mentioned, the invention also relates to pharmaceutical compositions containing one or more compounds of formula (I) as active ingredient, said compositions being administered by the intra nasal, oral or parenteral route in daily dosages ranging from 1 to 20 mg/kg body weight.

What is claimed is:

1. Compounds of formula (I)

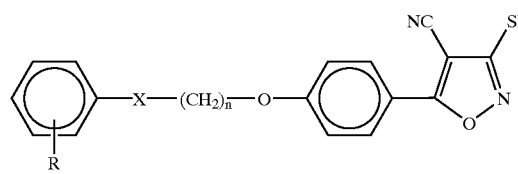

(I)

wherein
R is hydrogen, halogen, COOH, COOR", $C_1$–$C_4$ alkyl, $NO_2$, OR", phenyl;
R' is $C_{1-4}$ alkyl, COOH, COOR"
R" is $C_{1-4}$ alkyl
X is an oxygen or sulfur atom or a single bond
n is an integer 1–6
with the proviso that when R' is $C_{1-4}$ alkyl, R is not hydrogen or $C_{1-4}$ alkyl.

2. Compounds as claimed in claim 1, in which R is in para position to X, and n=2–4.

3. A compound according to claim 1 selected from the group consisting of:
3-methylthio-5-[4-[2-(4-nitrophenoxy)ethoxy]phenyl]-4-isoxazolecarbonitrile,
ethyl-4-[[2-[4-(3-methylthio-4-cyano-5-isoxazolyl)-phenoxy]-ethyl]-oxy]benzoate, and
3-methylthio-5-[4-[2-(4-bromophenoxy)ethoxy]phenyl]-4-isoxazolecarbonitrile.

4. A process for the preparation of the compounds according to claim 1 which process comprises reacting intermediates of formula (II) with a 3-R'S-substituted 5-(4-hydroxyphenyl)-4-isoxazolecarbonitrile of formula (IV) according to the scheme:

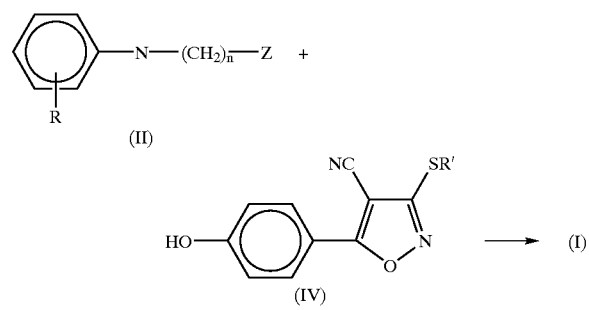

wherein R, R', X and n have the meanings defined above, whereas Z is a halogen atom.

5. A pharmaceutical composition having antiviral activity against the Polio 1, Echo 9, Coxsachie $B_1$, Measles and Rhino HRV2, HRV9, HRV14, HRV15, HRV29, HRV70, HRV86, HRV89 and HRV 1B viruses containing as an active ingredient a compound according to claim 1 together with a pharmaceutically acceptable carrier.

6. A method for treating a patient against infection from viruses selected from the group consisting of Polio 1, Echo 9, Coxsackie $B_1$, Measles, and Rhino Serotypes HRV2, HRV9, HRV14, HRV15, HRV29, HRV70, HRV86, HRV89 and HRV 1B which comprises administering to said patient an effective amount of a compostion according to claim 5.

7. A process according to claim 4 in which the halogen is bromine.

* * * * *